United States Patent [19]

Okumura et al.

[11] 4,284,831
[45] Aug. 18, 1981

[54] PROCESS FOR THE PRODUCTION OF TERTIARY ALCOHOLS

[75] Inventors: Yoshiharu Okumura, Kawagoe; Katsumi Kaneko, Ooi, both of Japan

[73] Assignee: Toa Nenryo Kogyo Kabushiki Kaisha, Tokyo, Japan

[21] Appl. No.: 146,443

[22] Filed: May 5, 1980

[30] Foreign Application Priority Data

Jun. 26, 1979 [JP] Japan .................. 54-79671

[51] Int. Cl.³ ............................................. C07C 29/04
[52] U.S. Cl. .................................. 568/899; 568/895; 568/896; 568/897; 568/898; 568/900; 568/901
[58] Field of Search .............. 568/899, 895, 896, 897, 568/898, 900, 901

[56] References Cited

U.S. PATENT DOCUMENTS

| | | | |
|---|---|---|---|
| 2,020,673 | 11/1935 | Dreyfus | 568/895 |
| 2,579,601 | 12/1951 | Nelson et al. | 568/896 |
| 3,088,969 | 5/1963 | Callahan et al. | 568/898 |
| 3,285,977 | 11/1966 | Henke et al. | 568/901 |
| 3,646,237 | 2/1972 | Horie et al. | |
| 3,651,165 | 3/1972 | Horie | |
| 3,965,039 | 6/1976 | Chaplits et al. | |
| 4,065,512 | 12/1977 | Carer | |
| 4,096,194 | 6/1978 | Moy et al. | 568/901 |

FOREIGN PATENT DOCUMENTS

| | | |
|---|---|---|
| 875,433 | 7/1979 | Belgium . |
| 1443009 | 7/1976 | United Kingdom . |
| 1443106 | 7/1976 | United Kingdom . |
| 1451158 | 9/1976 | United Kingdom . |
| 1518461 | 7/1978 | United Kingdom . |
| 2003141 | 7/1979 | United Kingdom . |

OTHER PUBLICATIONS

Odioso et al., "I. & E.C.", vol. 53, No. 3, Mar. 1961, pp. 209–211.
Cope, "J. Chem. and Eng. Data", vol. 11, No. 3, Jul. 1966, pp. 379–383.

*Primary Examiner*—Joseph E. Evans
*Attorney, Agent, or Firm*—Rebecca Yablonsky

[57] ABSTRACT

Tertiary alcohols are produced by the hydration of an isoolefin in the presence as catalyst of an acidic cation exchange resin such as a sulfonated styrene-divinylbenzene copolymer and in the presence of an oxy acid or lactone thereof such as γ-valerolactone. The process is useful for separating isobutylene from a hydrocarbon mixture containing its isomers via preparation of the alcohol, separation from the unreacted hydrocarbons and dehydration of the tertiary butyl alcohol to isobutylene.

10 Claims, 1 Drawing Figure

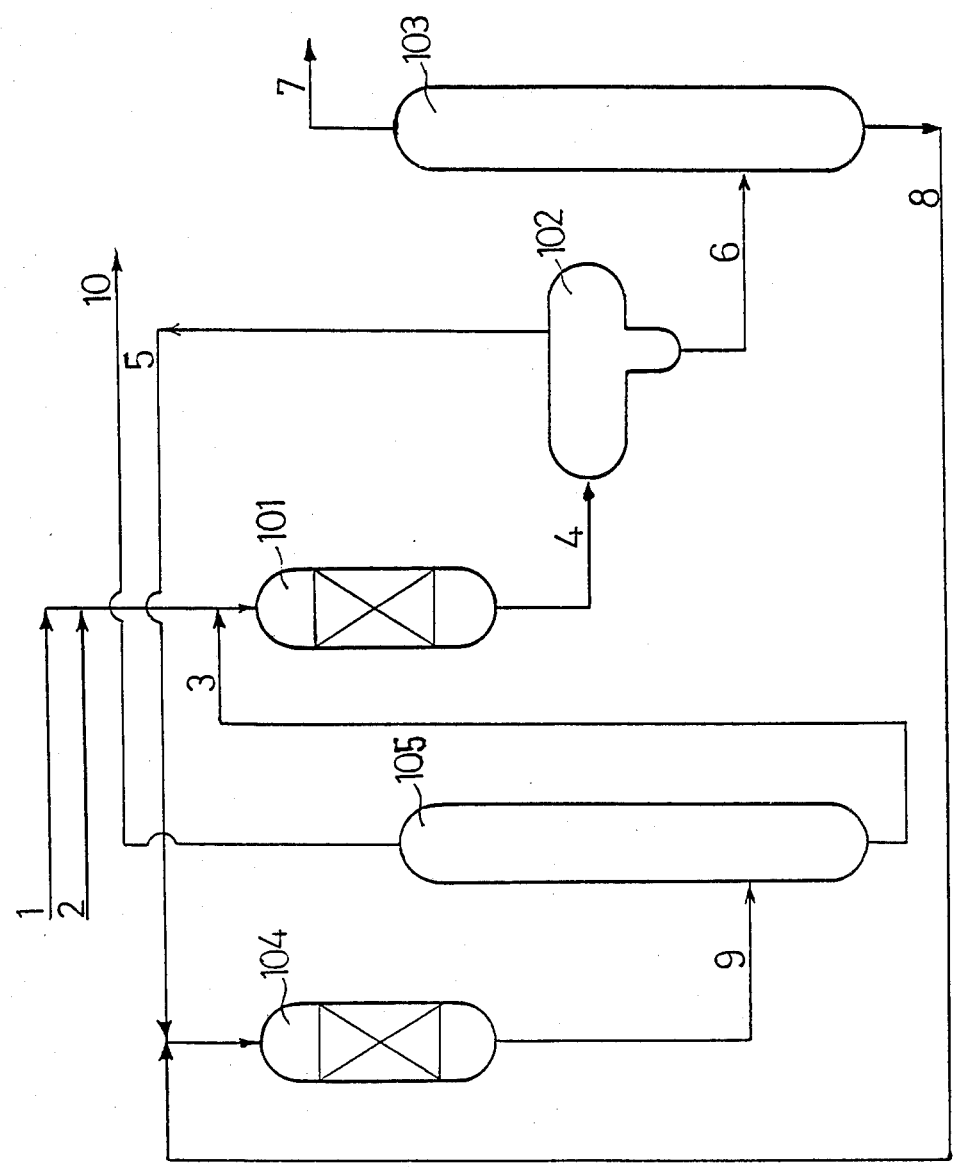

PROCESS FOR THE PRODUCTION OF TERTIARY ALCOHOLS

BACKGROUND OF THE INVENTION

1. Field of the Invention

This invention relates to a process for producing tertiary butyl alcohol (TBA) in a higher yield than previously obtainable by reacting isoolefins, in particular isobutylene, with water and more particularly it is concerned with a process for producing TBA in a higher yield by reacting isobutylene with water in the presence of an oxy acid or its derivative using a solid catalyst, preferably, an acid-type cation exchange resin.

2. Description of the Prior Art

For the production of TBA by hydration of isobutylene, there have been proposed an indirect hydration method comprising absorbing isobutylene in sulfuric acid and hydrolyzing the formed sulfuric acid ester and a direct hydration method comprising using a solid acid or an acidic aqueous solution as a catalyst.

Of these methods, the method using an aqueous solution of sulfuric acid has the disadvantage that large amounts of by-products are formed through dimerization or trimerization of isobutylene and that there are problems of the corrosion of the apparatus and the treatment of the waste sulfuric acid. In most of the direct hydration methods using a solid acid or acidic aqueous solution as a catalyst, on the other hand, some activity appears only at a high temperature such as about 200° C. or higher. Since the equilibrium of the hydration reaction is disadvantageous for the formation of the alcohol with the rise of temperature, it is necessary to conduct the reaction under a very high pressure in order to obtain a sufficient yield at such a high temperature. In this respect, a sulfonic acid-type ion exchange resin is a good catalyst capable of advancing the reaction at a relatively low temperature and low pressure. A number of methods using the same have been proposed.

For example, "Industrial and Engineering Chemistry" Vol. 53, No. 3, page 209-211 describes a method wherein isobutylene is continuously hydrated using an ion exchange resin as a catalyst, but this method is not always satisfactory because water and isobutylene form a heterogeneous system and thus give an insufficient reaction speed and yield. For the purpose of solving this problem, there have been proposed a method comprising reacting isobutylene or an isobutylene-containing hydrocarbon with an aqueous solution of an organic acid using an acidic ion exchange agent as a catalyst (Japanese Patent Application (OPI) No. 32116/1975 and Japanese Patent Publication No. 14044/1978); a method comprising carrying out the reaction with addition of a monohydric alcohol to the reaction system and using a similar catalyst (Japanese Patent Application (OPI) No. 137906/1975) and a method comprising carrying out the reaction with addition of glycol, glycol ether or glycol diether to the reaction system (Japanese Patent Application (OPI) No. 59802/1976 and U.S. Pat. No. 4,096,194).

In these methods for producing TBA by directly hydrating isobutylene, some improvement in reaction rate is found but, on the other hand, by-products are formed such as adducts of isobutylene with organic acids or organic solvents which are added to the reaction system. These by-products and organic solvents added to the reaction system make it difficult to separate and purify TBA by distillation utilizing the difference of their boiling points. In the case of using organic acids such as acetic acid, the apparatus tends to become corroded.

SUMMARY OF THE INVENTION

Applicant has made various studies to solve the above described problems and has found that the side reactions can be suppressed and the reaction rate and conversion ratio can be markedly promoted by adding an oxy acid or derivative thereof to water in the hydration reaction using an acid-type cation exchange resin. The present invention is based on this finding.

That is to say, the present invention provides a process for producing TBA comprising reacting $C_4$ or $C_5$ isoolefin or an isoolefin-containing hydrocarbon mixture, preferably isobutylene or an isobutylene-containing hydrocarbon mixture, with water in the presence of a solid catalyst, preferably an acid-type cation exchange resin, characterized that an oxy acid or derivative thereof is included in the reaction system.

The quantity of isobutylene or the isobutylene content in an isobutylene-containing hydrocarbon mixture, used in the present invention, is not particularly limited. Generally, the isobutylene-containing hydrocarbon mixture comprises predominantly $C_4$ hydrocarbons, for example, isobutylene, n-butylene and butane and, optionally, some amounts of $C_3$ or $C_5$ hydrocarbons. On a commercial scale, isobutylene-containing $C_4$ hydrocarbon mixtures obtained by steam cracking or catalytic cracking of petroleum fractions, are used.

BRIEF DESCRIPTION OF THE DRAWING

The accompanying drawing is a flow diagram which illustrates carrying out the process of the present invention continuously.

DETAILED DESCRIPTION

The oxy acid or derivative thereof used in the present invention is illustrated in the following:

Examples of the oxy acid are $C_2-C_5$ oxy acids such as oxyacetic acid (HOCH$_2$COOH), lactic acid (CH$_3$CH(OH)COOH), 3-oxypropionic acid (HOCH$_2$CH$_2$COOH), $\beta$, $\beta$, $\beta$-trichlorolactic acid (Cl$_3$CCH(OH)COOH), oxypivalic acid (HOCH$_2$C(CH$_3$)$_2$COOH), $\gamma$-oxybutryic acid (HOCH$_2$CH$_2$CH$_2$COOH) and the like.

As a typical example of the derivative of hydroxy acids, lactones corresponding to the intramolecularly condensed hydroxy acids are preferable, but other oxy acid esters may be used particularly the lower alkyl esters such as the methyl and ethyl esters. Useful examples of the lactone are $\beta$-propiolactone

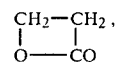

$\beta$, $\beta$-dimethylpropiolactone

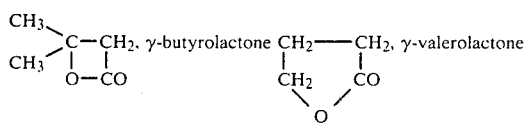

-continued

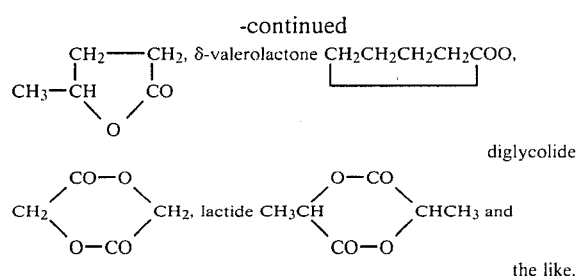

the like.

Useful examples of the oxy acid esters are glycolic acid methyl ester HOCH$_2$COOCH$_3$, glycolic acid ethyl ester HOCH$_2$COOC$_2$H$_5$ and the like. Thus the oxy acids particularly of C$_2$–C$_5$, straight or branched-chain alkyl type, and the derivatives thereof, viz., the oxy acid lower alkyl esters, the lactones, lactides, the halogen, especially chlorine, substituted derivatives, or mixtures of these, may be employed.

The oxy acid or derivative thereof is ordinarily used in the form of a solution in water, but it is not always required that it should be completely dissolved therein. As the added quantity of the oxy acid or derivative thereof is increased, in general, the rate of formation of TBA increases but if too large an excess is added, the efficiency of a reactor is lowered. Accordingly, the said compound is generally added in a proportion of 0.1 to 200 parts, preferably 0.3 to 50 parts by weight, to 1 part by weight of water.

The solid catalyst used in the present invention includes preferably strongly acidic cation exchange resins, for example, sulfonated polystyrene resins in which sulfonic acid groups are introduced into a base of a copolymer of styrene and divinylbenzene; phenolsulfonic acid resins in which sulfonic acid groups are introduced into a condensate of phenol and formaldehyde; and perfluorosulfonic acid resins consisting of copolymers of sulfonated vinyl ether fluoride and fluorocarbon, which are preferably of a gel type, macroporous type of macroreticular type. Supported ion exchange resins may be used. In addition, other solid catalysts for hydration can be used, for example, oxide type catalysts such as alumina, silica alumina, silica gel, zeolites, mordenites, kaolin; oxides of metals such as tungsten, thorium, zirconium, molybdenum, zinc, titanium and chromium; supported ones of these oxides; mineral acid catalysts such as supported phosphoric acid; heteropoly acid catalysts such as supported silicotungstic acid; sulfides such as sulfides of nickel and nickel-tungsten or supported ones of these sulfides.

The quantity of the catalyst depends upon how it is used, that is, whether it is used in the form of a suspension or a fixed bed. In the former case, the quantity of the catalyst is preferably 0.1 to 10% by weight of an aqueous solution of an oxy acid or derivative thereof.

The molar ratio of water to isobutylene ranges preferably from 1 to 10 since if less than 1, the conversion ratio is lowered, while if too large, the efficiency of a reactor is lowered.

The reaction temperature is generally 30° to 150° C., preferably 50° to 120° C.

The reaction pressure may be normal pressure, but the reaction is preferably operated under a pressure corresponding to the vapor pressure of a hydrocarbon mixture as starting material at the reaction temperature or under a pressure somewhat higher than the vapor pressure.

The form of a reactor to be used may be of a batch type, but in general, it is of a continuous type using an acid-type cation exchange resin in the form of a fixed bed.

The reaction time is generally in the range of 20 minutes to 10 hours in the case of a batch type and a suitable liquid hour space velocity (LHSV) of a hydrocarbon is ordinarily 0.3 to 10 hr$^{-1}$ in the case of a continuous type.

One embodiment of the process of the present invention will now be illustrated with reference to the accompanying drawing. In this embodiment, isobutylene form an isobutylene-containing hydrocarbon mixture is continuously converted into TBA and separated.

The system comprises mainly first and second hydration reactors 101 and 104 filled with a catalyst, a separator 102 for the separation of an unreacted hydrocarbon layer and aqueous layer, a distilling column 103 for the separation and recovery of TBA and a distilling column 105 for the separation of unreacted hydrocarbons.

To the first hydration reactor 101 are respectively fed a starting hydrocarbon mixture from a pipe line 1, water from a pipe line 2 and an aqueous solution containing an oxy acid or derivative thereof and TBA from a pipe line 3. The reaction liquor is fed to the separator 102 via a pipe line 4 from the bottom of the first hydration reactor 101. From the separator 102, the separated hydrocarbon mixture containing unreacted isobutylene is withdrawn via a pipe line 5 and fed to the second hydration reactor 104 with an aqueous solution containing the oxy acid or derivatives thereof via a pipe line 8. The reaction liquor containing TBA is discharged from the bottom of the second hydration reactor 104 and fed through a pipe line 9 to the distilling column 105, from which an unreacted hydrocarbon mixture is withdrawn via a pipe line 10 at the top and the aqueous solution containing the oxy acid or derivative thereof and TBA is taken via the pipe line 3 at the bottom, which is again fed to the first hydration reactor 101. The aqueous solution containing TBA and the oxy acid or derivative thereof, separated in the separator 102, is fed via a pipe line 6 to the distilling column 103, from which crude TBA is recovered via a pipe line 7 at the top and the aqueous solution containing the oxy acid or derivative thereof is withdrawn via the pipe line 8 at the bottom, followed by feeding again to the second hydration reactor 104. Removal of water from the crude TBA is carried out in conventional manner.

According to the process of the present invention, the rate of the hydration reaction of isobutylene and the conversion ratio thereof can be increased markedly with suppression of side reactions, thus allowing obtaining TBA in high yield. Moreover, an oxy acid or derivative having a much higher boiling point than TBA can readily be separated by distillation and thus the reuse thereof is simplified.

By means of the present process isobutylene can be isolated from an isobutylene-containing hydrocarbon mixture. That is to say, isobutylene in an isobutylene-containing hydrocarbon mixture is preferentially converted into TBA according to this process and the unreacted hydrocarbon mixture is then separated, after which TBA is dehydrated in known manner to give isobutylene. Isobutylene of high purity can be obtained in this way.

The present invention will further be illustrated in detail by the following examples and comparative examples, in which percentages are by mole.

EXAMPLES 1-12

With the use of an autoclave equipped with a stirrer and a cation exchange resin of highly porous type consisting of a sulfonated styrene-divinylbenzene copolymer as a catalyst, hydration reactions of isobutylene (99.5%) and an isobutylene-containing $C_4$ hydrocarbon (isobutylene 41.0%, n-butylenes 43.0%, butanes 16.0%) were carried out with solutions of oxy acids or derivatives thereof in water under conditions as shown in Table 1. After the reactions, the reaction products were rapidly cooled and subjected to analysis by gas chromatography to obtain the yields of TBA and by-products. The results are shown in Table 1.

TABLE 1

| Ex. | Oxy Acid Or its Derivative | Amount Of Oxy Acid or its Derivative (g) | Water (g) | Isobutylene Content in Starting Material (%) | Amount of Isobutylene (mol) | Amount of Catalyst (g) | Reaction Temperature (°C.) | Reaction Pressure (Kg/cm²) | Reaction Time (hr) | Yield of TBA (%) | Yield of By-products (%) |
|---|---|---|---|---|---|---|---|---|---|---|---|
| 1 | δ-Valerolactone | 200 | 200 | 99.5 | 3.0 | 20 | 80 | 12 | 0.5 | 39.7 | 0.2 |
| 2 | γ-Oxybutric Acid | 250 | 150 | 99.5 | 3.0 | 10 | 70 | 9 | 0.5 | 37.3 | 0.2 |
| 3 | γ-Valerolactone | 350 | 50 | 41.0 | 1.5 | 10 | 70 | 9 | 0.5 | 28.1 | 0.1 |
| 4 | γ-Valerolactone | 392 | 8 | 41.0 | 0.5 | 5 | 70 | 9 | 0.5 | 24.6 | 0.1 |
| 5 | γ-Butyrolactone | 300 | 100 | 99.5 | 3.0 | 10 | 70 | 9 | 0.5 | 25.3 | <0.1 |
| 6 | γ-Butyrolactone | 375 | 25 | 41.0 | 1.5 | 5 | 70 | 9 | 0.5 | 15.3 | 0.1 |
| 7 | γ-Butyrolactone | 200 | 200 | 41.0 | 1.5 | 20 | 80 | 12 | 1.0 | 38.2 | 0.1 |
| 8 | β-Propiolactone | 100 | 300 | 99.5 | 3.0 | 20 | 80 | 12 | 1.0 | 26.7 | 0.1 |
| 9 | 3-Oxypropionic Acid | 150 | 250 | 99.5 | 3.0 | 10 | 80 | 12 | 1.0 | 21.6 | 0.2 |
| 10 | γ-Valerolactone | 200 | 200 | 99.5 | 3.0 | 20 | 80 | 12 | 4.0 | 92.5 | 0.3 |
| 11 | γ-Butyrolactone | 375 | 25 | 41.0 | 0.75 | 10 | 80 | 12 | 5.0 | 88.7 | 0.2 |
| 12 | γ-Butyrolactone | 300 | 100 | 41.0 | 1.5 | 20 | 60 | 7 | 5.0 | 84.0 | 0.2 |

(Note) Yield: mole % based on isobutylene fed

COMPARATIVE EXAMPLES 1-7

In the hydration reaction of isobutylene with the same reactor, catalyst and starting hydrocarbon as those of Examples 1-12, comparison tests were carried out with no addition of organic solvent and with addition of organic solvents in place of the oxy acids or derivatives thereof. The experimental conditions and results are shown in Table 2.

The yields of TBA and by-products were obtained in a manner analogous to Examples 1-12.

TABLE 2

| Comparative Ex. | Solvent | Amount of Solvent (g) | Water (g) | Isobutylene Content in Starting Material (%) | Amount of Isobutylene (mol) | Amount of Catalyst (g) | Reaction Temperature (°C.) | Reaction Pressure (Kg/cm²) | Reaction Time (hr) | Yield of TBA (%) | Yield of by-products (%) |
|---|---|---|---|---|---|---|---|---|---|---|---|
| 1 | No | — | 400 | 99.5 | 3.0 | 20 | 80 | 12 | 1.0 | 8.5 | 0.5 |
| 2 | No | — | 400 | 41.0 | 1.5 | 15 | 80 | 12 | 8.0 | 25.8 | 1.3 |
| 3 | Methanol | 200 | 200 | 99.5 | 3.0 | 20 | 80 | 12 | 1.0 | 16.9 | 4.6 |
| 4 | Ethyl Cellosolve | 200 | 200 | 99.5 | 3.0 | 20 | 80 | 12 | 1.0 | 10.9 | 2.4 |
| 5 | Acetic Acid | 200 | 200 | 99.5 | 3.0 | 20 | 80 | 12 | 1.0 | 17.5 | 2.5 |
| 6 | Methyl Acetate | 200 | 200 | 99.5 | 3.0 | 20 | 80 | 12 | 1.0 | 18.1 | 1.5 |
| 7 | Ethyl Acetate | 50 | 350 | 99.5 | 3.0 | 20 | 80 | 12 | 1.0 | 10.1 | 0.6 |

(NOTE) Yield: mole % based on isobutylene fed

EXAMPLE 13

This example describes a process comprising continuously hydrating isobutylene in an isobutylene-containing $C_4$ hydrocarbon mixture and separating TBA using the apparatus shown in the accompanying flow diagram.

To a first hydration reactor 101 were respectively fed a starting hydrocarbon mixture (isobutylene content: 36.2%) via a pipe line 1 at a rate of 1000 mols/hr., water via a pipe line 2 at a rate of 527 mols/hr. and an aqueous solution of TBA and γ-butyrolactone (TBA: 17.6%; water: 18.7%; γ-butyrolactone: 63.7%) via a pipe line 3 at a rate of 471 mols/hr. The reaction mixture from the first reactor 101 was separated into a hydrocarbon layer and an aqueous layer in a separator 102. To a second hydration reactor 104 were respectively fed the hydrocarbon layer (isobutylene content: 12.4%) at a rate of 729 mols/hr and aqueous solution of γ-butyrolactone (γ-butyrolactone content: 63.7%) at a rate of 471 mols/hr. The first and second hydration reactors were filled with the same catalyst of the sulfonic acid-type cation exchange resin as that of Examples 1-12. In the first hydration reactor 101, a temperature of 90° C. and LHSV of 4 hr$^{-1}$ were maintained and in the second hydration reactor 104, a temperature of 70° C. and LHSV of 2 hr$^{-2}$ were maintained. The reaction mixture from the second hydration reactor 104 was fed to a distilling column 105 from which unreacted hydrocarbons (isobutylene content: 1.1%) were separated and recovered at a rate of 645 mols/hr. The aqueous layer in the separator 102 was fed to a distilling column 103 for the separation of TBA from which crude TBA (TBA content: 67.4%) was recovered at a rate of 527 mols/hr. The yield of TBA from the isobutylene in the starting hydrocarbon mixture was 98.1%.

What is claimed is:

1. In a process for the production of tertiary alcohols by causing an isoolefin or a hydrocarbon mixture containing an isoolefin to react with water in the presence of an acidic cation exchange resin, the improvement which comprises carrying out the reaction in the presence of an oxy acid ester selected from the group consisting of glycolic acid methyl ester and glycolic acid ethyl ester.

2. In a process for the production of tertiary alcohols by causing an isoolefin or a hydrocarbon mixture containing an isoolefin to react with water in the presence of an acidic cation exchange resin, the improvement which comprises carrying out the reaction in the presence of a C$_2$ to C$_5$ oxy acid or the lactones, lactides, methyl or ethyl esters thereof, or mixtures thereof.

3. In a process for the production of tertiary alcohols by causing an isoolefin or a hydrocarbon mixture containing an isoolefin to react with water in the presence of an acidic cation exchange resin, the improvement which comprises carrying out the reaction in the presence of an oxy acid selected from the group consisting of oxyacetic acid, lactic acid, 3-oxypropionic acid, β, β, β-trichlorolactic acid, oxypivalic acid and γ-oxybutyric acid.

4. In a process for the production of tertiary alcohols by causing an isoolefin or a hydrocarbon mixture containing an isoolefin to react with water in the presence of an acidic cation exchange resin, the improvement which comprises carrying out the reaction in the presence of a lactone selected from the group consisting of β-propiolactone, β,β-dimethylpropiolactone, γ-butyrolactone, γ-valerolactone and γ-valerolactone.

5. In a process for the production of tertiary alcohols by causing an isoolefin or a hydrocarbon mixture containing an isoolefin to react with water in the presence of an acidic cation exchange resin, the improvement which comprises carrying out the reaction in the presence of a lactide selected from the group consisting of diglycolide and lactide.

6. The process as set forth in claims 3, 4 or 5 in which the hydrocarbon mixture comprises predominantly C$_4$ hydrocarbons including isomers of isobutylene.

7. The process as set forth in claims 3, 4 or 5 in which the resin used is a sulfonated resin.

8. The process as set forth in claims 3, 4 or 5 in which the resin used is a sulfonated styrene-divinylbenzene copolymer.

9. The process as set forth in claims 3, 4 or 5 in which the feeds contains isobutylene and tertiary butyl alcohol is recovered as product.

10. The process as set forth in claims 3, 4 or 5 in which the feed comprises isobutylene in a hydrocarbon mixture, the resin used is a sulfonated styrene-divinylbenzene copolymer and tertiary butyl alcohol produced by hydration is recovered in a substantially purified form.

* * * * *